United States Patent [19]

Ali et al.

[11] Patent Number: 4,687,758
[45] Date of Patent: Aug. 18, 1987

[54] DES-PROLINE-N-METHYLARGININE VASOPRESSINS

[75] Inventors: Fadia E. Ali, Cherry Hill, N.J.; William F. Huffman, Malvern, Pa.; Garland R. Marshall, Clayton, Mo.; Michael L. Moore, Media, Pa.

[73] Assignee: SmithKline Beckman Corporation, Philadelphia, Pa.

[21] Appl. No.: 799,718

[22] Filed: Nov. 19, 1985

[51] Int. Cl.$^4$ ............ A61K 37/34; C07K 7/16
[52] U.S. Cl. ............ 514/11; 530/315; 514/807
[58] Field of Search ............ 530/315; 514/11, 807

[56] References Cited

U.S. PATENT DOCUMENTS

| | | | |
|---|---|---|---|
| 4,481,193 | 11/1984 | Ali et al. | 424/177 |
| 4,481,194 | 11/1984 | Ali et al. | 424/177 |
| 4,543,349 | 9/1985 | Callahan et al. | 530/315 |
| 4,599,324 | 7/1986 | Ali et al. | 514/11 |
| 4,604,378 | 8/1986 | Callahan et al. | 530/315 |

Primary Examiner—Delbert R. Phillips
Attorney, Agent, or Firm—Mark R. Daniel; Janice E. Williams; Alan D. Lourie

[57] ABSTRACT

Peptides having vasopressin antagonist activity are prepared by a peptide synthesizer to insert a N-methylarginine at the 7-position of the structure. An example of this series of compounds is [1-($\beta$-mercapto-$\beta,\beta$-cyclopentamethylenepropionic acid)-2-(O-ethyl-D-tyrosine)-4-valine-7-desproline-8-N-methylarginine-9-desglycine]-vasopressin.

8 Claims, No Drawings

DES-PROLINE-N-METHYLARGININE VASOPRESSINS

This invention relates to cyclic peptides which have vasopressin antagonist activity whose structures are distinguished by having a vasopressin antagonist six unit ring with a des-proline-N-methylarginine side chain.

BACKGROUND OF THE INVENTION

Earlier, we filed and issued two related patents on 7-des-proline-vasopressin antagonists, U.S. Pat. Nos. 4,481,193 and 4,481,194, both filed on Mar. 7, 1984 and issued on Nov. 6, 1984.

Recently, one of us filed another patent application, U.S. Ser. No. 747,640, covering potent vasopressin antagonists whose structures are distinguished by having two arginine-like units in the side chain which may be, in turn, optionally N-methylated. The present invention was conceived and reduced to practice earlier.

Peptide chemists recognize that N-methylamino acid units in a peptide chain exert a conformational effect on the preceding amino acid unit. Whether this unnatural positioning will exert an influence on biological activity is unpredictable.

The compounds disclosed in this application have been found to retain potent vasopressin antagonist activity, in fact, to have enhanced activity when compared with their des-N-methyl congeners.

In the description herein and in the claims, the nomenclature common in the art of peptide and vasopressin chemistry is used. When no configuration is noted, the amino acid unit is in the L, or naturally occurring, form. In certain structural formulas, the thio members of the Pmp and Cys units are added for clarity.

Certain of the peptide art designations used herein are the following: Pmp, β-mercapto-β,β-cyclopentamethylenepropionic acid; Tmp, β-mercapto-β,β-cyclotetramethylenepropionic acid; Tyr(Alk), O-alkyltyrosine; Abu, α-amino-n-butyric acid; Gly, glycine; Tyr, tyrosine; Phe, phenylalanine; Phe(Alk), 4-alkylphenylalanine; Val, valine; Ile, isoleucine; MeArg, N-methylarginine; Asn, asparagine; Tos, tosylate; BHA, benzhydrylamine; DMAP, 4-dimethylaminopyridine; DIEA, diisopropylethylamine; HF, hydrogen fluoride; 4-MeBzl, 4-methylbenzyl; TFA, trifluoroacetic acid; DCC, dicyclohexylcarbodiimide; Boc, t-butyloxycarbonyl; Z, benzyloxycarbonyl; VSP, vasopressin; HBT, hydroxybenzotriazole; ACM, acetamidomethyl.

In the definitions such as MeArg above, Me denotes a methyl located on the amido nitrogen of the peptide unit concerned.

"Alk" represents a lower alkyl of 1–4 carbons. For example, these may be optionally attached to the oxygen substituent of a tyrosine unit at position 2, especially at the 4′-position of the tyrosine unit, at the 4′-position of the phenylalanine unit at position 2 or at the terminal amido nitrogen (A) of the tail. Such alkyl substituents include methyl, ethyl, n-propyl, isopropyl or butyl. In the 2-tyrosine or 2-phenylalanine units, ethyl is preferred.

DESCRIPTION OF THE INVENTION

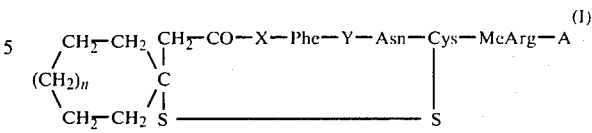

in which:
X is a D or L isomer of Tyr, Tyr(Alk), Ile, Phe or Phe(Alk);
n is 0 or 1;
Y is Val or Abu; and
A is $NH_2$, OH, Gly(OH) or Gly($NH_2$).

A subgeneric group of these compounds are those of formula I in which X is D-Tyr(Alk) and Y is Val.

Also included in this invention are pharmaceutically acceptable salts, complexes or prodrugs. The latter are esters of the acidic compounds of this invention when A is OH or Gly(OH).

The nontoxic, pharmaceutically acceptable acid addition salts are prepared in standard manner in a suitable solvent using the parent basic peptide with an excess of an acid, such as hydrochloric, hydrobromic, sulfuric, phosphoric, acetic, maleic, succinic, ethanedisulfonic or methanesulfonic acids. The acetate salt forms are often isolated directly. The ester derivatives or alkali metal salts of the acid forms of the end products, such as the methyl, ethyl or benzyl esters as well as the sodium or potassium salts are also easily prepared as known to the art.

The end products (I) of this invention are prepared by oxidation of the following linear heptapeptide:

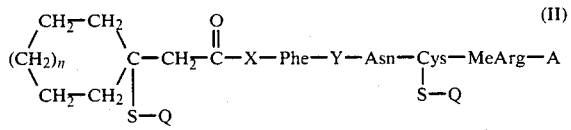

in which n, X, Y, and A are as defined for formula I above. The mercapto groups are members of the units at positions 1 and 6. Each Q is hydrogen or a displaceable protective group such as acetamidomethyl (ACM). The dithiol of formula II may be also oxidized in the form of an ester or amide derivative of the end unit at position 7 or 8. For example, the amide may be those peptides of Formula II in which A is —NHAlk or —$NH_2$. The prodrug esters, for example, would have A as OAlk or OBzl.

Said oxidation is carried out using an excess of an alkali metal ferricyanide, such as potassium or sodium ferricyanide, with the linear intermediate II. A suitable unreactive solvent, preferably an aqueous-miscible solvent at a neutral pH, about 7–7.5, is used. Reaction is carried out at ambient temperature or lower until the reaction is substantially complete. Preferably, the concentrations of the linear peptide dimercaptan and the oxidizing agent are low, say 0.01–0.1 molar concentration of oxidizing agent in several liters of aqueous solution to cyclize 1–5 grams of dimercaptan.

Other mild oxidation agents having an oxidation potential roughly equivalent to ferricyanide may also be used for the ring closure reaction. Oxygen passage through the reaction solution for several days, diiodoethane, iodine in methanol, hydrogen peroxide or oxidation in the presence of cupric salts are such alternatives.

Cyclization, also, occurs when a displaceable, thiol-protective group such as that at the mercaptan group of the Pmp unit is displaced intramolecularly.

An especially useful thio protective group is acetamidomethyl (ACM). Iodine/alcohol is used for direct, one-pot cyclization of the bis-S-ACM linear peptide.

Of course, one skilled in the art will recognize that certain cyclization methods are not appropriate if an interfering reaction site is present in the structure of the starting material of formula II. The linear mercaptan starting material may have common protective groups temporarily present at the various linear units.

The peptide chain of the linear peptides is usually built up, stepwise, proceeding from the A unit and working toward the Pmp unit. Each unit is properly protected as known in the peptide art and as described below. The sequence of step-reactions is conveniently carried out in a Beckman 990B peptide synthesizer or its equivalent without isolation of each intermediate peptide. The details of the procedure are in the working examples presented hereinafter.

The various amino acids (AA), which are consecutively added to the resin-supported chain, are protected as known to the art. For example, the Boc protecting group is used for an amino group, especially at the α-position; an optionally substituted benzyl, for the mercapto groups at the Pmp or Cys units; tosyl for the MeArg unit; and an optionally substituted carbobenzyloxy (Z) for the Tyr units. The protective groups are, most conveniently, those which are not easily removed by using mild acid treatment, such as for removing the Boc group. Rather, one should use HF, sodium-liquid ammonia or, for benzyl or carbobenzyloxy groups, catalytic hydrogenation.

The resin supported peptide is treated with an excess of anhydrous hydrogen fluoride with an appropriate scavenger compound, such as anisole, to give the linear peptide intermediate of formula II in good yield.

The end compounds of the invention have vasopressin antagonist activity. Vasopressin is known to contribute to the anti-diuretic mechanism of action within the kidney. When the action of these compounds antagonizes that of the natural anti-diuretic hormone (ADH), the body excretes water due to an increased permeability of the terminal portions of the renal tubule. The mechanism of action is at the vasopressin receptors ($V_2$-receptors) located on the plasma membrane of certain renal epithelial cells. The most notable pharmacodynamic effect of the ADH antagonists of the invention is that of a water diuretic rather than of a natriuretic such as hydrochlorothiazide.

Any patient suffering from the syndrome of inappropriate antidiuretic hormone secretion (SIADH) or from an undesirable edematous condition is a target for the claimed compounds. Examples of clinical conditions indicated for the compounds of this invention include hypertension, hepatic cirrhosis, hyponatremia, congestive heart failure or a component of any traumatic condition resulting from serious injury or disease.

The second group of vasopressin receptor sites are the vascular pressor sites ($V_1$-receptors) within the cardiovascular system itself. These may also be somewhat antagonized by the compounds of this invention.

The compounds of this invention, therefore, are used especially to induce anti-hypertensive or diuretic activity in patients in need of such treatment. The latter comprises the administration internally, that is, parenterally, buccally or by insufflation, of a nontoxic but effective quantity of the chosen compound, preferably dispersed in a pharmaceutical carrier. Dosage units of the active ingredient are selected from the range of 0.01 to 10 mg/kg, preferably 0.1 to 1 mg/kg, of base based on a 70 kg patient. The dosage units are administered to the human or animal patient from 1 to 5 times daily.

The pharmaceutical composition, which contains an active antagonist ingredient of formula I, comprises a dosage unit which is dissolved or suspended in a standard liquid carrier, such as isotonic saline, and is contained in an ampoule or a multiple dose vial suitable for a parenteral injection such as for intravenous, subcutaneous or intramuscular administration. A composition for insufflation may be similar but is usually administered in a metered dose applicator or inhaler. Pulverized powder compositions may, also, be used along with oily preparation, gels, buffers for isotonic preparations, buccal losenges, trans-dermal patches and emulsions or aerosols.

$V_2$-antagonistic activity toward the natural anti-diuretic hormone (anti-ADH activity) is determined, in vitro, in the medullary tissue of hog or human kidneys and, in vivo, in the hydropenic rat. The in vitro assay procedures for vasopressin stimulated adenylate cyclase activation or vasopressin binding activity are described by F. Stassen et al., J. Pharmacology and Experimental Therapeutics, 223, 50–54 (1982). $V_1$-antagonistic activity is determined by procedures using the rat thoracic aorta tissue and plasma membranes of rat liver. These procedures are described in the noted Stassen publication and in a publication at the 1st International Conference on Diuretics, Miami, Fla., March (1984).

The assay for anti-ADH activity in vivo is the hydropenic rat protocol described below:

Hydropenic Rat Screen

Food and water are removed from male rats approximately 18 hours prior to testing. Animals are housed 4 per metabolism cage. At 0 hour, the test compound is administered intraperitoneally to the test group and an equivalent volume of vehicle is administered to both control groups (fasted and non-fasted). Urine volume and osmolality are measured every hour for 4 hours. Test values are recorded as ml of urine excreted (cumulative), mEg/rat electrolyte excreted, mg/rat urea excreted, and osmolality in milli-Osmoles/Kg $H_2O$. A tolerance test is used to determine significance. $ED_{300}$ is defined as the dose of compound (μg/kg) required to lower urine osmolality to 300 m-Osmoles/kg.

TABLE 1

Pmp—D-Tyr(Et)—Phe—Val—Asn—Cys—X

|  | $K_b$ (nM) | | $K_i$ (nM) | $ED_{300}$ (μg/kg) | |
| --- | --- | --- | --- | --- | --- |
| (A) X = MeArg(NH$_2$) | 3.2 | (2) | 1.4 | 24.5 | (2) |
| (B) X = Arg(NH$_2$) | 9.1 | | 2.5 | 58 | (3) |

The two compounds in Table 1 have the same ring members. Comparison is thereby made between a species of this invention (A) and the earlier reported compound closest to it in structure (B). These data demonstrate compound A to be about twice as active in standard in vitro and in vivo protocols. The single digits are the number of tests.

The following examples are intended solely to teach the preparation and use of the compounds of this invention. All temperatures are in degrees Centigrade.

EXAMPLE 1

Preparation of Boc-MeArg(Tos)

To a solution of N$^{G\text{-}tosylarginine}$ (14.75 g, 44.9 mmol) in 65 ml of methanol was added sodium cyanoborohydride (1.98 g, 31.4 mmol) followed by benzaldehyde, (5.25 g, 49.5 mmol). The mixture was stirred at room temperature under argon for 18 hours. N$^\alpha$-Benzyl-N$^G$-tosylarginine precipitated and was collected by filtration to give 9.55 g (50.8%); m.p. 160°–167°.

To 8.35 g (2.0 mmol) of finely powdered N$^\alpha$-benzyl-N$^G$-tosylarginine, formic acid (95–97%) (2.3 ml, 60 mmol) and formaldehyde (37–40%) (1.95 ml, 24 mmol) were added. The reaction mixture was heated on a steam bath for 10 minutes, then concentrated in vacuo to a gummy material. The structure was confirmed to be N$^{\alpha\text{-}benzyl\text{-}N\alpha\text{-}methyl\text{-}NG}$-tosylarginine by FAB mass spectrum and NMR analysis.

To a solution of the N$^\alpha$-benzyl-N$^\alpha$-methyl-N$^G$-tosylarginine (2.0 mmol) in glacial acetic acid (50 ml), a mixture of water (10 ml) and 3N hydrochloric acid (5 ml) was added, then a catalytic amount of 5% palladium-on-carbon. The mixture was hydrogenated on a Parr shaker for about 6 hours for complete uptake of hydrogen. The catalyst was removed by filtration. The filtrate was concentrated to an oil. The oil residue was taken into water (20 ml), then neutralized to pH 7.03 (ammonia) to give a white solid. The solid was filtered off and recrystallized from hot water twice to give 2.5 g of N$^\alpha$-methy-N$^G$-tosylarginine; m.p. 210°–216° (decomposed). The structure was confirmed by NMR and MS analysis: $[\alpha]_D^{25}$ (0.1 MeOH) +5.0°; $[\alpha]_D^{25}$ (1N HCl) +20.9°; Calc'd for $C_{14}H_{22}N_4O_4S.H_2O$: C, 46.65; H, 6.71; N, 15.55. Found: C, 46.64; H, 6.70; N, 15.02.

MeArg(Tos) (2.5 g, 7.3 mmol) was dissolved in sodium hydroxide solution (0.3 g in 1 ml of water), and t-butyl alcohol (1.5 ml). To this clear solution was added di-tert.-butyldicarbonate (1.75 g, 8.03 mmol) slowly with good stirring. After a short induction period, the temperature rose from 23° to 28°. The reaction was brought to completion after the addition of another 1.15 ml of tert.-butyl alcohol and stirring overnight. The reaction mixture was worked up by adding water (10 ml) then extracted with hexane (3×10 ml). The aqueous solution was acidified with 1.0 g of potassium hydrogen sulfate while cooling to pH 2.2. It was then filtered to separate 2.5 g of solid which was recrystallized from ethyl acetate-hexane mixture to give Boc-MeArg(Tos): 1.37 g, m.p. 80°–84° (dec.). Calcd. for $C_{19}H_{30}N_4O_6S.0.5\ H_2O$: C, 50.54; H, 6.92; N, 12.41. Found: C, 50.82, 50.59; H, 6.81, 6.71; N, 12.26, 12.21; $[\alpha]_D^{25}$ (0.1 MeOH) −17.6°.

Pmp—Ile—Phe—Abu—Asn—Cys—MeArg—Gly(NH$_2$)

For the solid-phase synthesis of the resin-supported peptide, Boc-Gly-resin (1.19 mmol/g of resin) is used as a starting material. It is prepared by reacting the symmetrical anhydride (Boc-Gly)$_2$O with the benzhydrylamine resin in dimethylformamide for two hours. The benzhydrylamine resin as the hydrochloride salt is pretreated as follows:

(1) Suspend in methylene chloride overnight.
(2) Wash with methylene chloride (4 times, 1 min.).
(3) Neutralize with 7% diisopropylethylamine (DIEA). in methylene chloride (2 times, 2 min.)
(4) Wash with methylene chloride (6 times, 1 min.).
(5) Wash with previously dried dimethylformamide (2 times, 1 min.).

The symmetrical anhydride, (Boc-Gly)$_2$O, and its resin form are prepared as follows:

To a solution of Boc-Gly(OH) (0.35 g, 2 mmol) in 10 ml of methylene chloride is added 1 ml (1 mmol) of dicyclohexylcarbodiimide in methylene chloride (1M solution). The mixture is rocked on a shaker for 10 minutes, then filtered. The solid is washed (3×1 ml) with methylene chloride. The filtrate is concentrated in vacuum (room temperature) to a volume of 0.5 ml. It is dissolved in dimethylformamide and added to the BHA resin. After a complete coupling (1–2 hrs.), the resin is washed with dimethylformamide (2×1 min.), followed by methylene chloride (4×1 min.). A quantitative ninhydrin test and an amino acid analysis are performed to calculate the percent loading on the resin.

The appropriately protected (Boc) amino acids are coupled sequentially on to the Boc-Gly-resin using the Beckman peptide synthesizer 990 B. The program used for each coupling, except Boc-Asn and Pmp(4-MeBzl), is as follows:

(1) Wash with $CH_2Cl_2$ (3 times, 1 min.).
(2) Prewash with 50% TFA in $CH_2Cl_2$ (1 time, 1 min.).
(3) Deprotection with 50% TFA in $CH_2Cl_2$ (30 min.).
(4) Wash with $CH_2Cl_2$ (3 times, 1 min.).
(5) Prewash with 7% DIEA in $CH_2Cl_2$ (1 time, 1 min.).
(6) Neutralize with 7% DIEA in $CH_2Cl_2$ (1 time, 10 min.).
(7) Wash with $CH_2Cl_2$ (3 times, 1 min.).
(8) Protected amino acid (3 mmol) in $CH_2Cl_2$, followed by addition of DCC, 3 mmol, 10 ml of 0.3 M in $CH_2Cl_2$, and coupling for two hours.
(9) Wash with $CH_2Cl_2$ (3 times, 1 min.).
(10) Wash with EtOH/$CH_2Cl_2$ 1:1 (3 times, 1 min.).
(11) Wash with $CH_2Cl_2$ (3 times, 1 min.).

In the case of coupling of Asn moiety, 1-hydroxybenzotriazole (HBT, 6 mmol) is used, 10 ml of 0.6 M in dimethylformamide. Dry dimethylformamide is also used as solvent when Pmp(4-MeBzl) is coupled onto the peptide resin, using 4-dimethylaminopyridine (3 mmol). Completion of each coupling reaction is monitored by the ninhydrin test. The 4-methylbenzyl group (4-MeBzl) is used to protect the thiol group of Cys, Tmp and Pmp moieties.

The resulting protected peptide resin intermediate i.e., [Pmp(4-MeBzl)-Ile-Phe-Abu-Asn-Cys(4-MeBzl)-MeArg(Tos)-Gly-BHA-Resin], is washed well with the methylene chloride and dried in vacuo overnight to give the resin-supported linear product.

Pmp(4-MeBzl)-Ile-Phe-Abu-Asn-Cys(4-MeBzl)-MeArg-(Tos)-Gly-BHA-Resin, 2.0 g, in 2.5 ml of anisole, is reacted with anhydrous hydrogen fluoride (25 ml) at 0° for 50 minutes. After evaporation in vacuo to dryness, the residue is treated with anhydrous ether and the crude peptide is extracted with degassed dimethylformamide (50 ml) and 33% acetic acid (50 ml) into 4 liters of water. The aqueous disulfhydryl linear peptide is cyclized using 0.01 M potassium ferricyanide solution at pH 7.2 until color persisted for 30 minutes. After the completion of the oxidation reaction, the pH of the solution is adjusted to pH 4.5 by adding glacial acetic acid. This solution is passed through a weakly acid acrylic resin (Bio-Rex 70) column (2.5×12 cm) slowly. The column is eluted with pyridine-acetate buffer (30:4:66, pyridine/acetic acid/water). The pyridine acetate solution is removed by distillation in vacuo. The residue is lyophilized from 1% acetic acid to give the titled peptide. Purification is carried out as in Example 3 below.

EXAMPLE 3

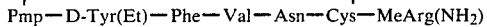
Pmp—D-Tyr(Et)—Phe—Val—Asn—Cys—MeArg(NH$_2$)

The protected peptide intermediate resin, Pmp(-4-MeBzl)-D-Tyr(Et)-Phe-Val-Asn-Cys(4-MeBzl)-N-MeArg(Tos)-BHA resin was prepared by the solid-phase method on 0.5 mmol of benzhydrylamine resin. All amino acids used in the synthesis were protected as Boc on the nitrogen and coupled sequentially using DCC/HBT. The Pmp(4-MeBzl) was coupled using DMAP. Boc-N-CH$_3$ Arg(Tos) was prepared as in Example 1. The peptide was cleaved from the resin with deprotection of the side chain protecting groups using anhydrous hydrogen fluoride (30 ml) and anisole (3 ml) at 0° for 60 minutes. After evaporation in vacuo to dryness, the residue was washed with anhydrous ether. The crude peptide was extracted with 50% degassed acetic acid (120 ml) into a 2l of degassed water at pH 4.5. The aqueous, disulfhydryl linear peptide was oxidatively cyclized with 70 ml of 0.01 M potassium ferrricyanide solution at pH 7.2. The pH of the solution was adjusted to 4.5 using glacial acetic acid. It was purified through a weakly ion-exchange column (Bio-Rex 70) to give 249 mg of partially purified, titled peptide.

Purification:
1. Partition column, Sephadex G-25, sample ~140 mg using n-butanol/acetic acid/water (B/A/W) (4:1:5) v/v to give fractions a, b and c.
   a: 46.16 mg
   b: 28.5 mg
   c: 18.85 mg
2. Gel filtration, Sephadex G-15, 0.2 M HOAc, used 46.16 mg from 1a to obtain:
   2a: 25.26 mg
   2b: 6.19 mg
   2c: 9.00 mg 2a of purity greater than 97% was submitted for biological testing.

Physical Data
M.F.: $C_{47}H_{69}N_{11}O_9S_2$, M.Wt.: 995.44,
FAB: (M+H)hu +996,
AAA: Asp (1.00); Cys (0.46); Val (1.04); Tyr (0.51); Phe (1.01),
(Note: MeArg cannot be detected on AA analyzer but its presence was confirmed by FAB (fast atom bombardment spectrum analysis).
Peptide content: 70.3%

Chromatography Data:
(1) Thin Layer Chromatography (TLC):
   a: B/A/W/E ethyl acetate (1:1:1:1) v/v R$_f$=0.64,
   b: B/A/W (4:1:5) v/v (upper phase) R$_f$=0.42.
(2) High Performance Liquid Chromatography (HPLC): Altex ultrasphere ODS column, 5μ, 4.5 max., 25 cm., solvent system 0.1% trifluoroacetic acid (a) and acetonitrile (b), (a) Gradient, 80%a : 20%b to 50:50 in 15 minutes, k'=6.5,
(b) Isocratic, 57%a : 43%b, k'=3.2.

The titled amide is in the form of the acetate salt. Other salts may be prepared by reacting the base form of the peptide in dimethylformamide with an excess of ethereal acid.

EXAMPLE 4

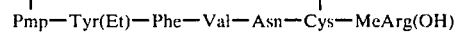
Pmp—Tyr(Et)—Phe—Val—Asn—Cys—MeArg(OH)

1.33 Grams of the MeArg(Tos) is dissolved in 10 ml of ethanol and 3 ml of water added. The pH is then adjusted to 7.1 with an aqueous solution of cesium bicarbonate.

The mixture is concentrated and the residue evaporated three times from 20 ml of toluene. This residue is, then, placed under high vacuum at ambient temperature overnight.

The salt is dissolved in 10 ml of dimethylformamide and 1 g of commercial chloromethylated polystyrene resin (1 eg. Cl) added. The mixture is stirred at 53° under argon overnight.

The mixture is filtered and the resin washed with dimethylformamide (5×20 ml), DMF/water, 9:1, (5×20 ml), DMF (5×20 ml) and ethanol (6×20 ml). It is, then, dried under high vacuum at ambient temperature over the weekend.

The peptide chain is built up in a Beckman synthesizer as described above using the Boc derivatives of Cys(4 MeBzl), Asn, Val, Phe, Tyr(Et) and the S-(4-MeBzl)Pmp derivative. The resin is removed, washed and dried in vacuo.

0.5 Mmol of the peptide resin is treated with 1.5 ml of anisole and stirred for 60 minutes at 0° in 15 ml of hydrogen fluoride. The hydrogen fluoride is, then, removed under water aspirator pressure at 0°.

The residue is then washed with 3×25 ml of ether (discarded) and the peptide eluted with dimethylformamide and 30% acetic acid (4×10 ml). This solution is added to 2 l of degassed water and the pH adjusted to 7.0 with ammonium hydroxide. A 0.01 M potassium ferricyanide solution is added slowly until a yellow color persists.

The pH is then adjusted to 4.5 with acetic acid and the mixture stirred for 30 minutes with 25 g (wet) of a weakly basic ion exchange resin. The suspension is filtered and the resin washed with 2×400 ml of 30% acetic acid.

The filtrate is, then passed through a $C_{18}$ flash column (7×16 mm). The column is washed with water (3×400 ml) and the peptide eluted with acetonitrile/water/TFA (50:50:0.25). The product bearing fractions are combined, concentrated and lyophilized to yield the titled free 7-MeArg(OH) peptide.

The MeArg acid in dimethylformamide is treated with sodium carbonate solution to form the sodium salt.

The MeArg acid is reacted with one equivalent of n-propylamine in the presence of DCC and HBT in dimethylformamide to produce the N-n-propyl derivative of the titled compound.

EXAMPLE 5

Using the synthetic methods disclosed above the following species are prepared:

Tmp—Tyr(Me)—Phe—Val—Asn—Cys—MeArg(NH2)

Pmp—D-Phe(Et)—Phe—Val—Asn—Cys—MeArg(NH2)

Pmp—D-Phe—Phe—Val—Asn—Cys—MeArg(OH)

Pmp—Phe(Me)—Phe—Val—Asn—Cys—MeArg—Gly(NH2)

EXAMPLE 6

Parenteral Dosage Unit Compositions:

A preparation which contains 0.10 mg of the cyclic peptide of Example 3 as a sterile dry powder for parenteral injection is prepared as follows: 0.10 mg of peptide amide is dissolved in 1 ml of an aqueous solution of 20 mg of mannitol. The solution is filtered under sterile conditions into a 2 ml ampoule and lyophilized. The powder is reconstituted before either intramuscular or intravenous injection to a subject suffering from edema susceptible to anti-ADH mechanism of action. The injection is repeated as necessary, from 1-5 times daily or in continuous i.v. drug injection. Other peptides of this invention are prepared and used in like manner.

Nasal Dosage Unit Compositions:

30 Mg of finely ground cyclic peptide of this invention such as the product of Example 3 is suspended in a mixture of 75 mg of benzyl alcohol and 1.395 g of a suspended agent such as a commercial mixture of semi-synthetic glycerides of higher fatty acids. The suspension is placed in an aerosol 10 ml container which is closed with a metering valve and charged with aerosol propellants. The contents comprise 100 unit doses which are administered intranasally to an edematous subject from 1-6 times a day.

What is claimed is:

1. A polypeptide compound having the formula:

$$\begin{array}{c} CH_2-CH_2 \quad CH_2CO-X-Phe-Y-Asn-Cys-MeArg-A \\ (CH_2)_n \quad C \\ CH_2-CH_2 \quad S-\!\!\!\!\!\!\!\!\!\!\!\!\!\!\!\!-S \end{array}$$

in which:
X is a D or L isomer of Tyr, Tyr(Alk), Ile, Phe or Phe(Alk);
n is 0 or 1;
Y is Val or Abu; and,
A is NH2, OH, Gly(OH) or Gly(NH2), or a pharmaceutically acceptable salt, ester prodrug or complex thereof.

2. The compound of claim 1 in which X is D-Tyr(Et).
3. The compound of claim 1 in which A is NH2.
4. The compound of claim 1 having the formula:

Pmp—D-Tyr(Et)—Phe—Val—Asn—Cys—MeArg(NH2)

or a pharmaceutically acceptable, acid addition salt thereof.

5. The compound of claim 1 having the formula:

Pmp—D-Tyr(Et)—Phe—Val—Asn—Cys—MeArg—Gly(NH2)

or a pharmaceutically acceptable, acid addition salt thereof.

6. A pharmaceutical composition comprising a pharmaceutical carrier and, dispersed therein, a vasopressin antagonistic but nontoxic quantity of a compound of claim 1.

7. A pharmaceutical composition comprising a pharmaceutical carrier and, dispersed therein, a vasopressin antagonistic but nontoxic quantity of the compound of claim 4.

8. The method of inducing a vasopressin antagonist effect in a patient in need thereof comprising administering internally to said patient a nontoxic, effective therefor quantity of a compound of claim 1.

* * * * *